United States Patent [19]

Welker

[11] Patent Number: 4,829,835
[45] Date of Patent: May 16, 1989

[54] ADJUSTABLE SAND RELIEF VALVE FOR SAND LADEN CRUDE OIL

[76] Inventor: Brian H. Welker, 13818 Florence Rd., Sugarland, Tex. 77478

[21] Appl. No.: 64,678

[22] Filed: Jun. 22, 1987

[51] Int. Cl.$^4$ .............................................. G01N 1/12
[52] U.S. Cl. ................................... 73/864.63; 73/155; 73/863.86; 73/864.62
[58] Field of Search ............... 73/863.86, 864.15, 155, 73/864.63, 864.62, 864.34, 864.35; 166/325, 326

[56] References Cited

U.S. PATENT DOCUMENTS

| 3,385,370 | 5/1968 | Knox et al. | 166/325 X |
| 3,970,106 | 7/1976 | Harris | 166/326 X |
| 4,046,011 | 9/1977 | Olsen | 73/864.35 |
| 4,403,518 | 9/1983 | Welker | 73/864.34 |
| 4,440,032 | 4/1984 | Welker | 73/864.34 X |
| 4,470,773 | 9/1984 | Welker | 73/864.62 X |
| 4,583,293 | 4/1986 | Smith | 73/864.63 X |
| 4,628,750 | 12/1986 | Welker | 73/864.63 |

Primary Examiner—Eugene R. Laroche
Assistant Examiner—Seung Ham

[57] ABSTRACT

For use in an oil sampler having a vanishing chamber, the vanishing chamber relatively opposite a reciprocating anvil, and wherein sampled oil is subject to including abrasive particles such as sand therein, a relief valve which comprises an in-line check valve connected serially downstream from the vanishing chamber, the relief valve including an axial flow passage terminating at a valve seat, and a movable valve element having a resilient plug insert which is larger in diameter than the valve seat which closes against the valve seat. The resilient plug is held in a surrounding metal skirt. A stem and coil spring guide the resilient plug to a closed position. When abrasive particles are delivered through the oil flow, they impinge against the resilient plug and avoid abrasion of the metal components around the valve seat. This then deflects the flow at reduced velocity into a larger surrounding chamber and thereby reduces downstream damage.

10 Claims, 2 Drawing Sheets

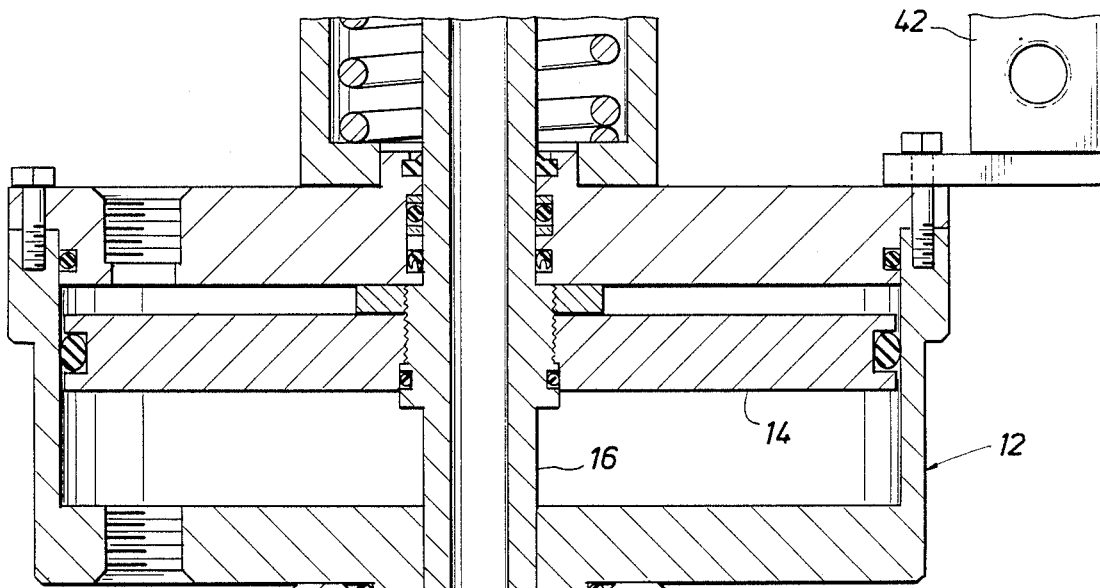
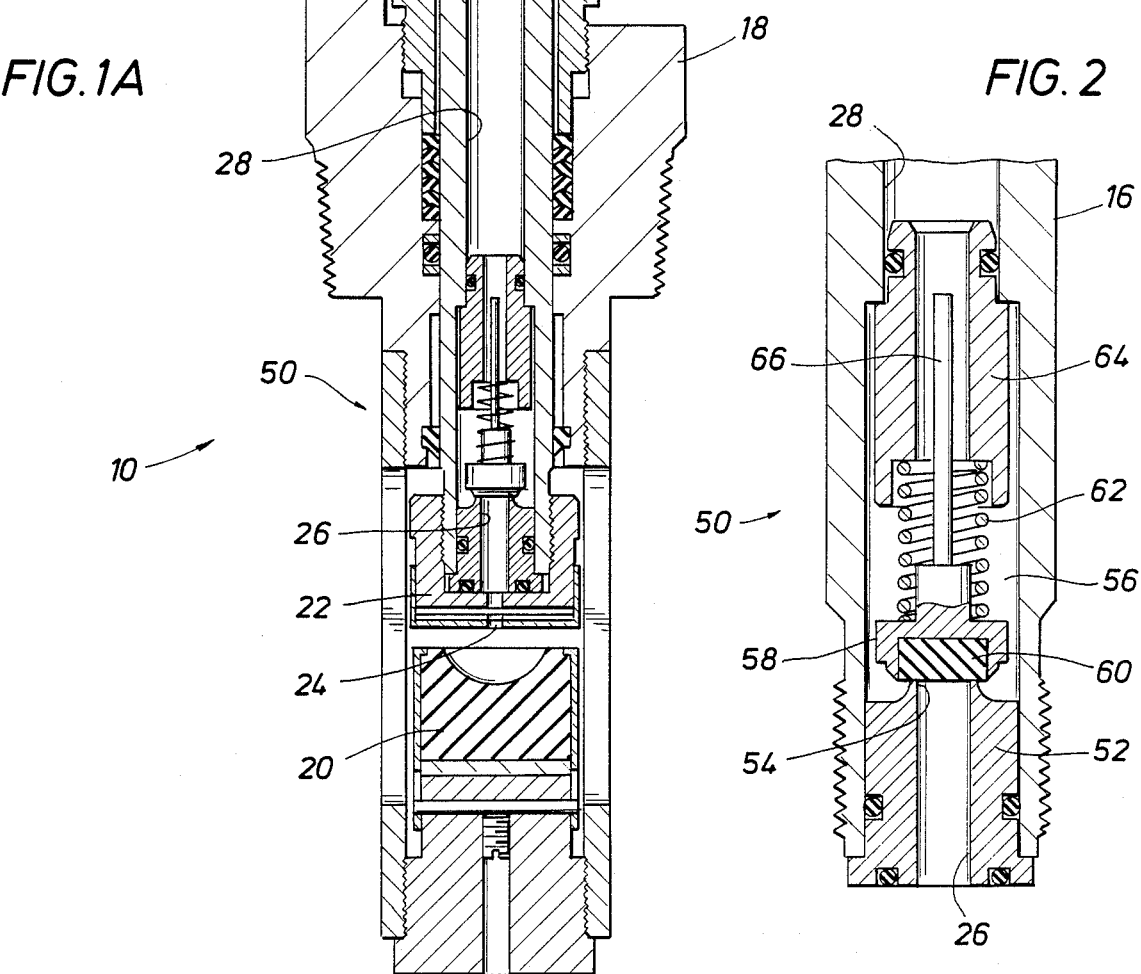
FIG.1A
FIG.2

ADJUSTABLE SAND RELIEF VALVE FOR SAND LADEN CRUDE OIL

BACKGROUND OF THE INVENTION

The present disclosure is directed to a sand relief valve which protects against erosion resulting from sand laden crude oil production. Production from an oil well may often include sand which has a tendency to cut, abrade or erode fittings of the apparatus handling the crude production. One important piece of apparatus is a sampling device which obtains a sample of produced oil. The sampling apparatus collects a certain portion of the produced oil and enables storage of this small portion in a separate sample container. The sample is useful in providing an assay of the produced oil. An assay is essential so that the cost of the oil can be determined based on the assay. Also, the chemical constituents which make up the oil are important. For these reasons, it is highly desirable to collect the sample from a large production stream. For instance, the production stream may be quite sizeable but the sample size permitted by the sample storage apparatus is much smaller. One such sampling apparatus is described in U.S. Pat. No. 4,440,032 assigned to the assignee of the present apparatus.

Sampling devices are thus subject to rapid damage if the oil is under substantial pressure and carries abrasive sand in it. The ability of the apparatus to last is in part determined by the volume of sand which is found in the produced oil. It is also partly dependent on the pressure, and is further dependent on other scale factors which may vary from time to time. Whatever the fact, the present apparatus is a protective valving system to be included in a sampler to thereby reduce damage arising from production of sand cut oil.

Flowing oil is ordinarily a good lubricator. This remains true until the flowing oil carries substantially quantities of sand in it. At that juncture, it can quickly erode the metal components which handle the oil and sand. This is especially true where the flow must pass through a valve seat or perhaps a nipple. It also is true where the flow must turn or is otherwise redirected. The abrasive particles carried in the flowing oil abrade the exposed metal surfaces and damage them. This is cumulative and can very quickly totally destroy an operative device such as a crude oil sampler system.

The present apparatus is a protective valving system incorporated in a crude oil sampler device. It is included in the system to prevent damage from sand laden oil flow. Moreover, this apparatus can be used to choke or restrict the flow velocity and thereby reduce downstream damage resulting from the flowing oil which is otherwise abrasive as a result of the sand particles carried in the oil. In one embodiment of the present apparatus, the crude oil sampler has a long or extended portion which is adapted to be attached to a pipeline or extend into some type of container. It has an internal reciprocating rod. The rod normally encloses an axial flow path. In this embodiment, a valve arrangement is placed in the reciprocating rod. It blocks the flow of the produced oil. This blocked flow impinges on a plug which is forced open in the fashion of a check valve. When open, flow through the valve continues but the flow velocity is reduced. The check valve element is exposed to the sand particles in the flowing oil. The present disclosure sets forth a protective valve which is constructed as a resilient insert within a surrounding valve element which is located so that the flowing sand particles impinge against the resilient insert.

In a second embodiment of the present apparatus, at the outlet of the sampling apparatus, a passage flowing therefrom is interrupted by a check valve apparatus. This check valve construction again imposes a valve element including a resilient insert. This construction enables the resilient insert to confront and block the sand particles and thereby avoid impingement against metal components and their consequential erosion. Both embodiments are spring adjustable to control the measure of opening.

DETAILED DESCRIPTION OF THE DRAWINGS

So that the manner in which the above recited features, advantages and objects of the present invention are attained and can be understood in detail, more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

FIGS. 1A and 1B are a continued sectional view through a crude oil sampler system which is constructed with the improved sand relief valve of the present disclosure located therein at two locations to thereby enable the device to handle crude oil production laden with sand;

FIG. 2 is an enlarged sectional view of a portion of the apparatus shown in FIG. 1A showing in detail the sand relief valve of the present disclosure.

DETAILED DESCRIPTION OF THE PREFERRED EMBODIMENT

Figure 1B:
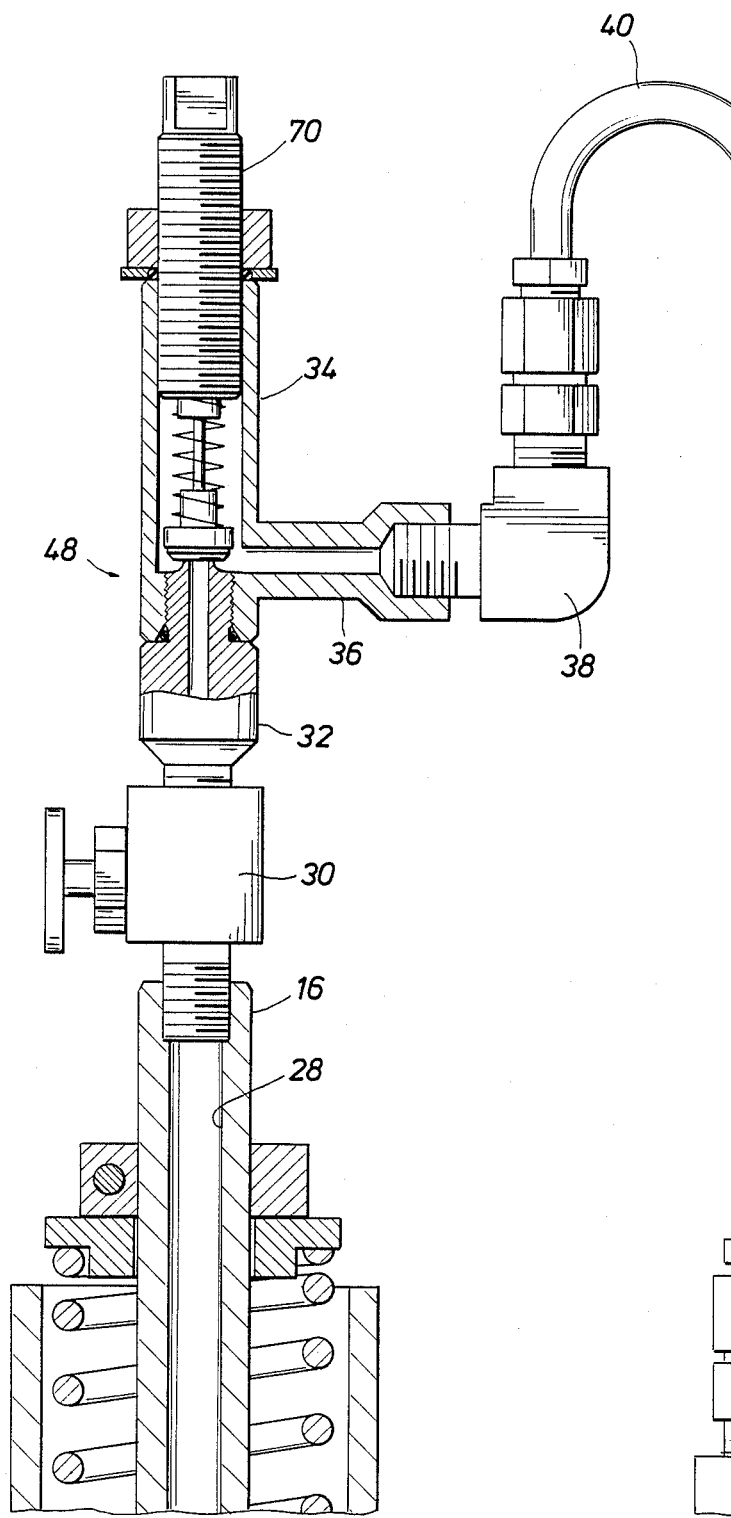

Attention is first directed to FIG. 1A of the drawings here the numeral 10 identifies a crude oil sampler in accordance with the present disclosure. Description of this sampler will be somewhat brief in view of the description that is set forth in the reference named above. However, a sufficient portion of the sampler will be described to locate the components of this device and to show how it produces crude oil which may be subject to entrainment of sand particles and which then is assisted in operation by the relief valve of the present disclosure. FIG. 1A shows a fluid motor, this being identified by the numeral 12, and having the preferred form of a piston motor. It is reciprocated by driving a diaphragm or piston 14 in reciprocating fashion. In turn, that reciprocates a piston rod 16. The piston rod extends out of the motor housing, and passes through a fitting 18 which enables the sampler 10 to be connected with a pipeline, an oil storage tank or the like. The fitting 18 is a cylindrical body which is constructed with threads matching those of a sized and threaded opening to permit assembly. The fitting 18 is hollow. It surrounds the reciprocating piston rod 16.

At the lower end of the apparatus, a resilient member 20 constructed with a hemispherical cavity at the top face is used to capture fluid to be sampled. It is located opposite a circular anvil 22. This is constructed of metal so that it moves against the resilient member 20, causing that head to collapse whereby oil captured in the hemisphere is pumped through a small opening at 24. The lower end of the apparatus is constructed with a surrounding cylindrical housing to enable the probe like member to be positioned in the oil containing pipeline or vessel.

The opening 24 is directed then to a passage 26. In turn, this communicates with a passage 28 which extends along the piston rod 16. There is a check valve arranged upstream of the opening 24. this assures that produced or sampled oil does not flow back out of the apparatus. After production, the oil from the sampler then flows along the passage 28.

Going now to FIG. 1B of the drawings, there it will be observed that the passage 28 extends along the rod 16 which is then exposed on the exterior of the equipment. Here, the rod 16 is hollow to the top end where the passage 28 terminates. A suitable valve 30 having a hand operated valve stem is installed to open or close and thereby deliver the produced oil. The valve 30 joins to a fitting 32 which in turn connects with a tee 34. The tee has a branch 36 to enable production to be conducted from the tee through an elbow 38 and then to a flexible delivery line 40. The delivery line 40 connects with an elbow 42 shown in both FIGS. 1A and 1B. The elbow 42 is fixed because it is anchored to the housing of the motor for the sampler pump 10. The delivery line 40 is made of flexible material. The pumping action reciprocates the rod 16 which in turn reciprocates the apparatus at the upper end of the sampling device 10. This is absorbed by flexure of the delivery line 40. Thus, the elbow 42 is anchored in place and delivers an outlet flow which is then delivered to some other line for accumulation in a sample storage vessel or the like.

Figure 3:
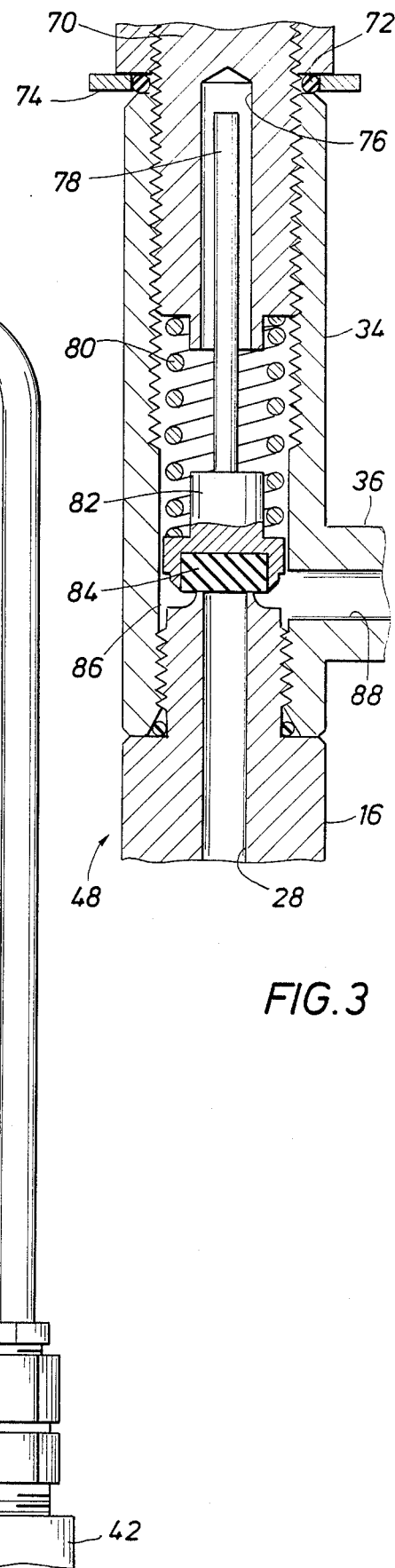
FIG. 3 shows an alternate embodiment of the sand relief valve of the present disclosure.

Returning now to FIG. 1A of the drawings, the numeral 50 generally identifies a relief valve constructed in accordance with the teachings of the present disclosure. A similar relief valve is also found at FIG. 1B and is identified by the numeral 48. The relief valve 50 will be described first as more fully detailed in FIG. 2 of the drawings. Thereafter, additional details will be given with respect to the relief valve 48 which is shown in FIG. 3. The relief valves 48 and 50 are similar in construction.

The relief valves of this disclosure, being the valves 48 and 50, are constructed downstream of the sampler head shown in the lower parts of FIG. 1A which includes the resilient plug and cooperative anvil which provides fluid in pumped strokes. The fluid flows along the passage and is delivered to the relief valves, first one and then the other. As shown in FIG. 2 of the drawings, the lower end of the apparatus is fixed in the sense that it is integral with the reciprocating rod 16. In other words, all the apparatus shown in FIG. 2 reciprocates together as a unit. The passage 26 opens upwardly through a central sleeve 52. That is joined to a surrounding elongate hollow cylindrical portion of the rod 16. Moreover, the sleeve 52 has an upper terminus or end 54. It opens outwardly into the enlarged chamber 56. The chamber is partially closed by a check valve body 58. It is constructed in the form of a circular member which is hollow at the center, being recessed to receive a resilient insert 60. The insert 60 is sized to be equal to and slightly larger than the diameter of the opposing passageway through which the sand laden oil must flow. The entire flow is directed against the resilient member. The resilient member is constructed with a width enabling the entire oil flow to be deflected. Such deflection dissipates a significant portion of the flow velocity. It causes the abrasive impact to be dissipated against the resilient plug. This dissipation of energy is accompanied by a reduction in abrasion on the other components downstream.

It has been discovered that the resilient member 60 has substantially greater life than a metal facing member. That is, the abrasion which is observed in this valve body is markedly reduced through the use of the resilient plug. The sand laden oil thus delivers a certain measure of kinetic energy on impact against the plug and is deflected radially outwardly into the larger chamber 56. It is then able to flow upwardly at a reduced velocity and has dissipated a portion of kinetic energy, decreasing the impact and impingement occurring downstream from the relief valve insert 60.

The apparatus also incorporates a spring 62 aligned against a tubular insert 64. There is a stem 66 which guides the valve element movement. There is no flow permitted until the spring force is overcome whereupon the spring 62 is compressed. Movement of the spring element is guided by stem 66. Flow continues upwardly in FIG. 2 and along the passage 28 previously defined.

Going now to FIG. 3 of the drawings, it will be recalled that the tee 34 incorporates the lateral branch 36. It is plugged at the top end by a threaded plug 70 shown both in FIGS. 1B and 3. The plug is locked in place and sealing is accomplished by a captured O-ring 72 with a surrounding lock ring 74. In turn, these secure the plug 70 at a specified depth in the tee. The plug 70 is axially drilled at 76, and aligns a stem 78. The stem is axially central of a compression spring 80 which operates in a fashion similar to the spring 62 just described. The spring bears against a valve body 82. The valve body supports an insert of resilient material at 84. The insert 84 is larger in diameter than the axial passage 28 which extends upwardly through the reciprocating rod 16 also shown in FIG. 3.

The resilient insert is larger in diameter so that the entire fluid flow impinges against the insert. The insert deflects the fluid flow, presumably carrying abrasive sand, radially outwardly into a surrounding chamber 86. The fluid flow is then directed to the side through the lateral passage 88. This continues on through the remainder of the apparatus discussed with regard to FIG. 1B of the drawings. The lateral passage carries away the flow. Again, the relief valve shown in FIG. 3 reduces the velocity and thereby dissipates the flow velocity. This reduces significantly the possibility of sand abrasion on the interior of the components in the system.

The relief valves shown in FIGS. 2 and 3 operate in similar fashion. In both instances, they are supported by a resilient mechanism which forces the valve elements against valve seats. This tends to close in the absence of flow. However, when flow occurs, the valve elements are then forced open. Moreover, the valve elements are able to move and are restored to their original position. Movement is guided by the valve stems which support the members. The valve stems are included to align the valve elements for certain return.

In the construction of the valve elements, it is desirable that the surrounding metal skirt be positioned away from the impinging flow. This assures that the entire flow in the sampler is directed against the resilient face only. The resilient member is preferably made of some elastomeric material. A suitable material is a closed cell polyurethane. There are other elastomers that can be used. The elastomeric material can be controllably cast to a desired depth and diameter. Likewise, the hardness can be adjusted. As a representative hardness, the resilient material is in the range of about 60-95 durometer on the Rockwell C scale. In part, the resilience can be varied over a wide range and is a function of several variables including size of the particles, the extent of sand flow in the oil, the flow velocity and the like. It is desirable generally to have a fairly large surrounding chamber which is approximately twice the diameter of the resilient insert. The resilient member is in turn larger than the diameter of the passage which confronts it.

In the disclosed sampler 10 of the present system, the relief valve is included at two separate locations. Service and accessibility is perhaps more easily accomplished with the location shown in FIG. 3. However, when the relief valve is located as shown at FIG. 2, it protects a larger portion of the components of the sampler. Thus, the internal location is perhaps more difficult to service, but is also more closely located at the point of ingress of the oil flow. To this end, it protects more of the system. When located as shown in FIG. 3, servicing is easily accomplished, but the components up to that location are less protected.

The springs can be adjusted to change the pressure drop. This can be adjusted by spring replacement. Another adjustment is simply adjustment of the compression of the spring and this is particularly permissible in the embodiment shown in FIG. 3. There, the plug which restrains the spring can be moved and thereby adjust the force required to open the relief valve.

While the foregoing is directed to the preferred embodiment, the scope thereof is determined by the claims which follow.

What is claimed is:

1. In a crude oil sampler subject to production of crude oil having abrasive particles flowing therein, and wherein the sampler has an anvil opposite a resilient plug having a hemispherical cavity therein and relative reciprocation occurs between the plug and anvil to provide fluid sample pumping from the resilient plug along a passage of the sampler, a relief valve serially communicated with the passage in which the fluid flow is directed, the relief valve comprising a valve seat at the end of said passage, and a resilient faced valve element means urged towards said valve seat wherein said resilient face comprises a face transverse to flow along said passage and wherein oil pressure forces the resilient faced valve element means from said valve seat and thereby directs abrasive particles flowing in the sampled oil against the resilient faced valve element means.

2. The apparatus of claim 1 wherein said valve element means includes a surrounding metal skirt with a circular resilient plug on the interior of said skirt and having an exposed face, and including a stem for guiding said valve element means for reciprocating movement of said resilient face toward said valve seat to position said resilient face transverse to said passage when closed.

3. The apparatus of claim 2 wherein said resilient element is made of an elastomeric material and has a hardness between about 60 to about 95 durometer.

4. The apparatus of claim 2 wherein said valve stem is positioned axially of a return spring, and said return spring urges said valve element towards a closed position.

5. The apparatus of claim 4 including an elongate sleeve in said passage terminating in said valve seat.

6. The apparatus of claim 5 including an internal cavity surrounding said valve seat larger in diameter than said valve seat and valve element means, said cavity being formed downstream of said valve seat and having a volume sufficient to receive said spring therein.

7. The apparatus of claim 6 wherein said cavity is located in a reciprocating rod in the sampler, and the rod delivers motion to the anvil and plug thereof, said rod having the passage therealong and locating said relief valve fluidly downstream of the anvil and plug.

8. The apparatus of claim 7 wherein said relief valve is supported between ends of the rod.

9. The apparatus of claim 7 wherein said relief valve is supported at an end of the rod.

10. The apparatus of claim 9 wherein said relief valve delivers oil into said cavity and then into a protruding lateral branch.

* * * * *